(12) United States Patent
Nakada et al.

(10) Patent No.: US 11,207,479 B2
(45) Date of Patent: Dec. 28, 2021

(54) CPAP DEVICE

(71) Applicant: NIDEC COPAL ELECTRONICS CORPORATION, Tokyo (JP)

(72) Inventors: Yuki Nakada, Sano (JP); Takatoshi Inoguchi, Sano (JP); Yasuhiro Tobinai, Sano (JP); Hiroki Matsushita, Sano (JP)

(73) Assignee: NIDEC COPAL ELECTRONICS CORPORATION, Tokyo (JP)

( * ) Notice: Subject to any disclaimer, the term of this patent is extended or adjusted under 35 U.S.C. 154(b) by 389 days.

(21) Appl. No.: 16/274,775

(22) Filed: Feb. 13, 2019

(65) Prior Publication Data

US 2019/0175854 A1 Jun. 13, 2019

Related U.S. Application Data

(63) Continuation of application No. PCT/JP2017/024024, filed on Jun. 29, 2017.

(30) Foreign Application Priority Data

Sep. 12, 2016 (JP) .............................. JP2016-177803

(51) Int. Cl.
*A61M 16/00* (2006.01)
*A61B 5/00* (2006.01)
(Continued)

(52) U.S. Cl.
CPC ....... *A61M 16/0066* (2013.01); *A61B 5/4818* (2013.01); *A61M 16/0069* (2014.02);
(Continued)

(58) Field of Classification Search
CPC . A61B 2560/0228; A61B 5/087; A61B 5/097; A61B 5/4836; A61M 16/00;
(Continued)

(56) References Cited

U.S. PATENT DOCUMENTS 4,425,840 A * 1/1984 Masao ................... F04D 29/703
454/285
6,126,721 A * 10/2000 Nemser ................. A61M 16/10
95/54
(Continued)

FOREIGN PATENT DOCUMENTS

CN 101205933 6/2008
GB 1119750 A * 7/1968 ........... F04D 29/526
(Continued)

OTHER PUBLICATIONS

International Search Report for international application PCT/JP2017/024024, dated Sep. 26, 2017.
(Continued)

*Primary Examiner* — Annette Dixon
(74) *Attorney, Agent, or Firm* — Burris Law, PLLC

(57) ABSTRACT

A fan unit produces an airflow. A pressure difference generating member causes a pressure difference in the airflow. A sensor detects a pressure difference between the air pressure on the upstream side of the pressure difference generating member and the air pressure on the downstream side thereof. A straightening plate is provided between the fan unit and the pressure difference generating member, and straightens the airflow produced by the fan unit. A straightening plate comprises a first fin and a second fin which are arranged along the airflow, and a lattice-like third fin which is arranged on the downstream side of the first fin and the second fin, and through which the airflow through the first fin and the second fin passes.

4 Claims, 10 Drawing Sheets

(51) Int. Cl.
*A61M 16/06* (2006.01)
*A61M 16/08* (2006.01)

(52) U.S. Cl.
CPC ....... *A61M 16/0666* (2013.01); *A61M 16/024* (2017.08); *A61M 16/0816* (2013.01); *A61M 2016/0027* (2013.01); *A61M 2016/0039* (2013.01); *A61M 2205/3334* (2013.01); *A61M 2205/42* (2013.01); *A61M 2205/502* (2013.01); *A61M 2205/8262* (2013.01); *A61M 2206/11* (2013.01)

(58) Field of Classification Search
CPC .......... A61M 16/0063; A61M 16/0066; A61M 16/0069; A61M 16/0072; A61M 16/0075; A61M 16/024; A61M 16/0672; A61M 16/10; A61M 16/101; A61M 16/107; A61M 16/12; A61M 16/142; A61M 16/204; A61M 16/205; A61M 2016/0021; A61M 2016/0027; A61M 2016/0033; A61M 2016/0039; A61M 2202/0208; A61M 2202/025; A61M 2202/0275; A61M 2205/3355; A61M 2205/3358; A61M 2205/3365; A61M 2205/3368; A61M 2205/3569; A61M 2205/52; A61M 2230/432; B01D 2313/16; B01D 2313/18; B01D 53/22; B01D 63/02; B01D 63/022; B01D 63/06; B01D 63/08; B01D 63/14; F04D 25/10; F04D 29/4246; F04D 29/444; F04D 29/526; F04D 29/582; F04D 29/646; F04D 29/661; F04D 29/664; F04D 29/703; F05D 2250/52; F25D 17/062; F25D 17/08; F25D 2317/063; F25D 2317/067; F25D 2317/0683; G01F 15/005; G01F 15/046; G01F 25/0007; H02K 1/187; H02K 11/33; H02K 15/12; H02K 5/08
See application file for complete search history.

(56) References Cited

U.S. PATENT DOCUMENTS

| | | | | |
|---|---|---|---|---|
| 7,044,129 | B1* | 5/2006 | Truschel | A61M 16/12 128/204.18 |
| 2006/0283450 | A1* | 12/2006 | Shissler | A61M 16/142 128/204.21 |
| 2007/0145842 | A1* | 6/2007 | Zhu | F04D 29/582 310/88 |
| 2015/0320954 | A1 | 11/2015 | Suzuki et al. | |
| 2016/0184539 | A1 | 6/2016 | Suzuki et al. | |
| 2017/0211438 | A1 | 7/2017 | Suzuki et al. | |
| 2018/0163748 | A1* | 6/2018 | Hayamitsu | F25D 17/08 |

FOREIGN PATENT DOCUMENTS

| | | |
|---|---|---|
| JP | H06241858 | 9/1994 |
| JP | H1048021 | 2/1998 |
| JP | 2001147012 | 5/2001 |
| JP | 2003185477 | 7/2003 |
| JP | 2004522487 | 7/2004 |
| JP | 2010117201 | 5/2010 |
| JP | 2010203415 | 9/2010 |
| JP | 2013150684 | 8/2013 |
| JP | 2015033522 | 2/2015 |
| JP | 2016034411 | 3/2016 |

OTHER PUBLICATIONS

Office Action issued in corresponding Japanese patent application 2016-177803, dated Jun. 9, 2020.
Office Action for corresponding CN Application No. 201780054557.5, dated Nov. 30, 2020.

* cited by examiner

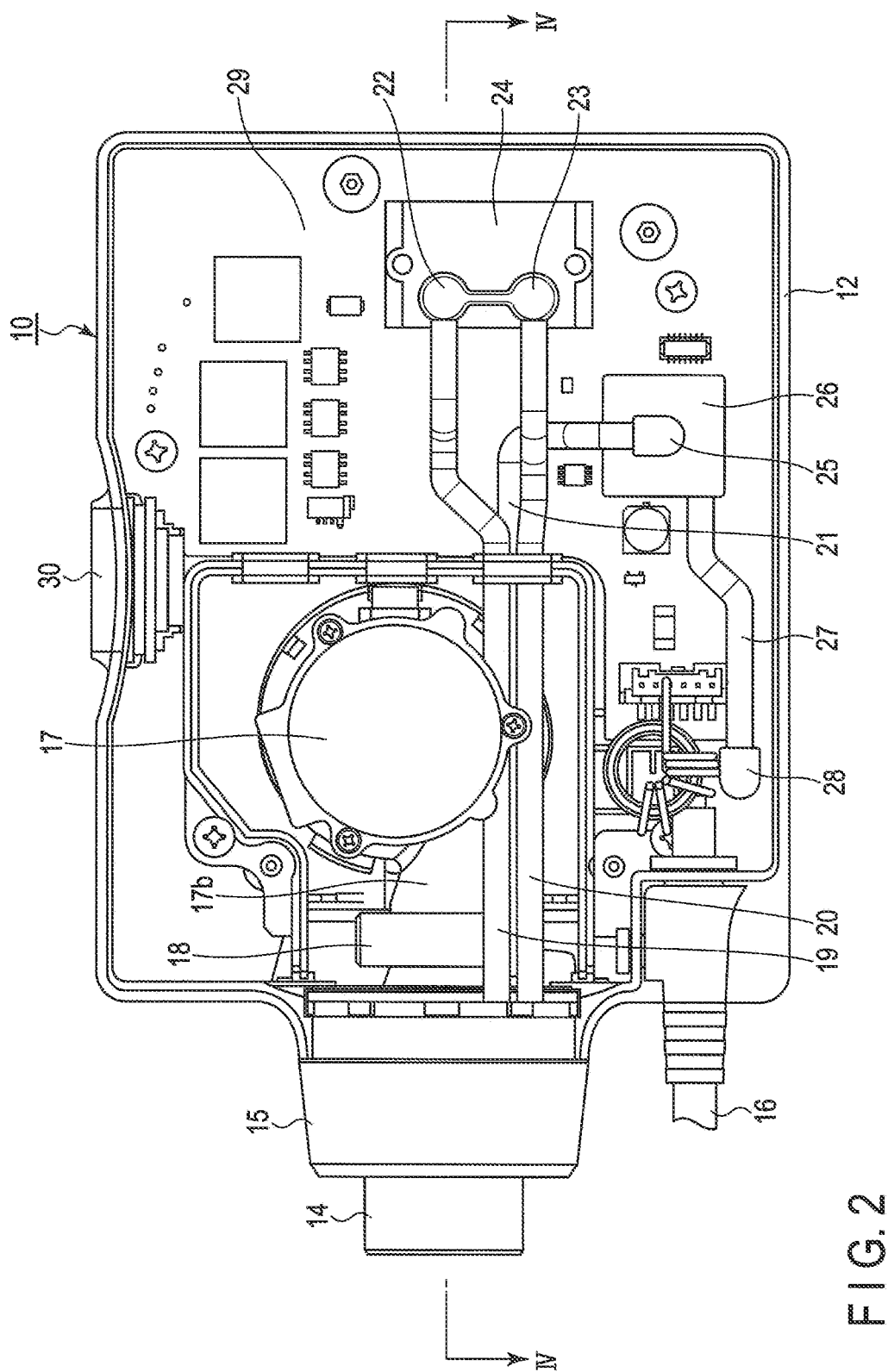
F I G. 2

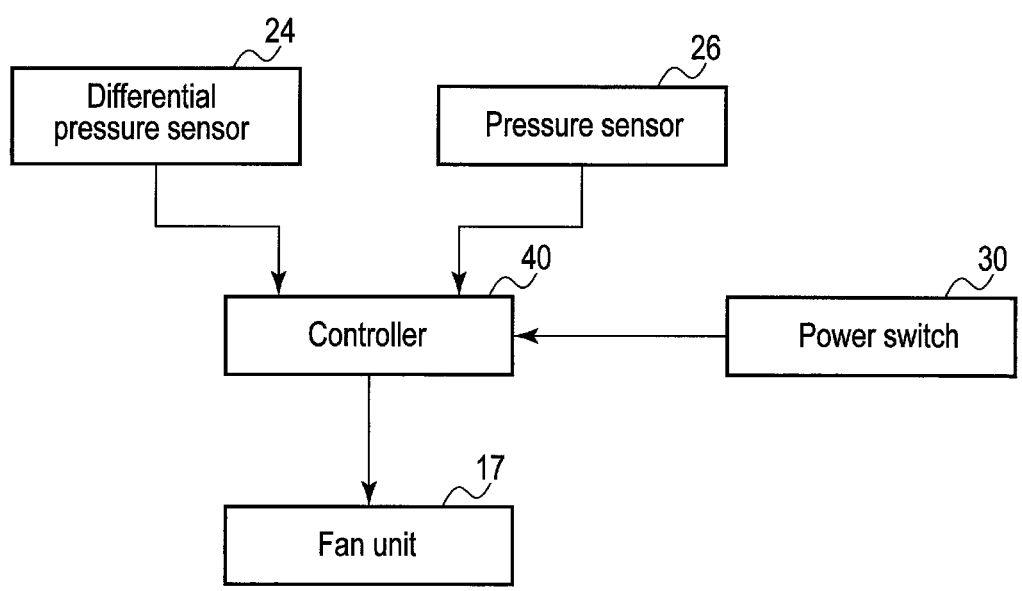
F I G. 3

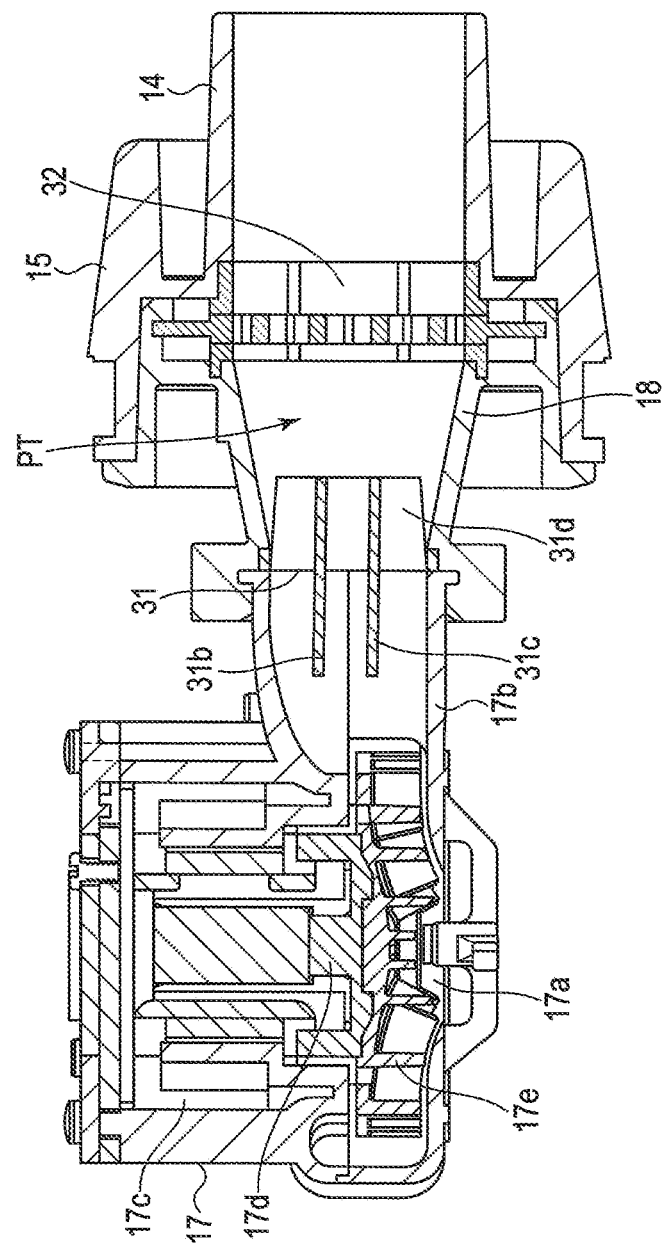
F I G. 4

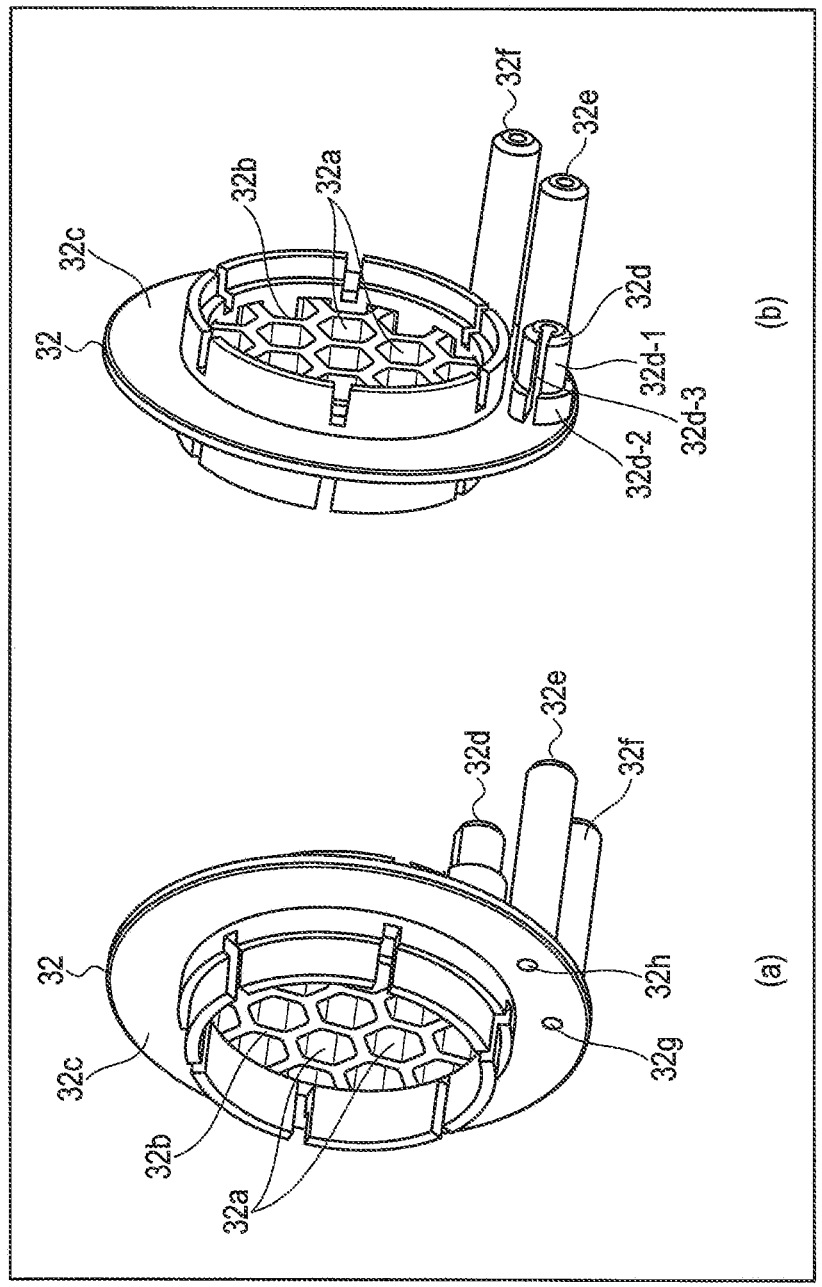
F I G. 6

CPAP DEVICE

CROSS-REFERENCE TO RELATED APPLICATIONS

This application is a continuation of International Application No. PCT/JP2017/024024, filed on Jun. 29, 2017, which claims priority to and the benefit of JP 2016-177803 filed on Sep. 12, 2016. The disclosures of the above applications are incorporated herein by reference.

FIELD

The present disclosure relates to a Continuous Positive Airway Pressure (CPAP) device to be applied to, for example, medical treatment for a sleep apnea syndrome.

BACKGROUND

The statements in this section merely provide background information related to the present disclosure and may not constitute prior art.

A CPAP device is a device configured to send an airflow of fixed pressure produced by a fan into the respiratory tract through a pipe and mask fitted on the nose of the patient or nasal cannula (for example, Patent Literature 1 (JP 2013-150684 A)).

The CPAP device is used for a patient in his or her sleep, and hence silence is required of the CPAP device. An airflow produced by a fan includes eddies, and hence noise is generated by the eddies. In order to prevent eddies from occurring and suppress noise, the CPAP device is provided with a straightening plate (for example, Patent Literature 2 (JP 2016-34411 A), Patent Literature 3 (JP 2004-522487 A)).

SUMMARY

In order to evaluate a dynamic respiratory event during CPAP treatment, it is necessary for the CPAP device to detect a flow rate of the airflow. In order to measure the flow rate of the airflow, a flow path resistance is set inside a flow path through which the air is made to flow, and a pressure difference between an upstream position and downstream position of the flow path resistance, i.e., differential pressure is detected by a sensor.

Heretofore, as the flow path resistance, as shown in Patent Literature 2, a straightening plate including a plurality of openings has been used. The straitening plate is configured to reduce eddies included in the airflow produced by the fan, and a pressure difference (hereinafter also referred to as differential pressure) between the airflow on the upstream side of the straightening plate and airflow on the downstream side of the straightening plate is detected by the sensor. However, although eddies included in the airflow on the downstream side of the straightening plate are reduced by the straightening plate, eddies included in the airflow on the upstream side of the straightening plate are not reduced by the straightening plate. For this reason, since the airflow on the upstream side of the straightening plate includes eddies, it is difficult to detect the pressure difference between the airflow on the upstream side of the straightening plate and airflow on the downstream side of the straightening plate with a high degree of accuracy.

In order to accurately detect the pressure difference between the airflow on the upstream side of the straightening plate and airflow on the downstream side of the straightening plate, it is possible to reduce the influence of the eddies on the upstream side of the straightening plate by providing the straightening plate at a position separate from the fan. However, in this case, the distance between the fan and straightening plate becomes larger, and hence it becomes difficult to downsize the CPAP device.

This embodiment provides a CPAP device small in size and capable of improving the detection accuracy of the sensor.

A CPAP device according to the embodiment comprises: a fan configured to produce an airflow; a pressure difference generating member configured to pass the airflow through and cause a pressure difference in the airflow; a sensor configured to detect a pressure difference between the air pressure on the upstream side of the pressure difference generating member and the air pressure on the downstream side of the pressure difference generating member; and a straightening plate provided between the fan and the pressure difference generating member and configured to straighten the airflow produced by the fan, wherein the straightening plate includes at least one fin arranged along the airflow, and a lattice-like fin which is arranged on the downstream side of the at least one fin, and through which the airflow passing through the at least one fin passes.

The present invention can provide a CPAP device small in size and capable of improving the detection accuracy of the sensor.

Further areas of applicability will become apparent from the description provided herein. It should be understood that the description and specific examples are intended for purposes of illustration only and are not intended to limit the scope of the present disclosure.

DRAWINGS

In order that the disclosure may be well understood, there will now be described various forms thereof, given by way of example, reference being made to the accompanying drawings, in which:

FIG. 2 is a top view showing the inside of the CPAP device shown in FIG. 1.

FIG. 3 is a block diagram schematically showing the configuration of the control system of the CPAP device according to the embodiment.

FIG. 4 is a cross-sectional view showing only the essential part along line IV-IV of FIG. 2.

FIG. 6 (a) is a perspective view showing a pressure difference generating member according to this embodiment, and FIG. 6 (b) is a perspective view showing the pressure difference generating member viewed from a direction different from FIG. 6 (a).

Figure 1:
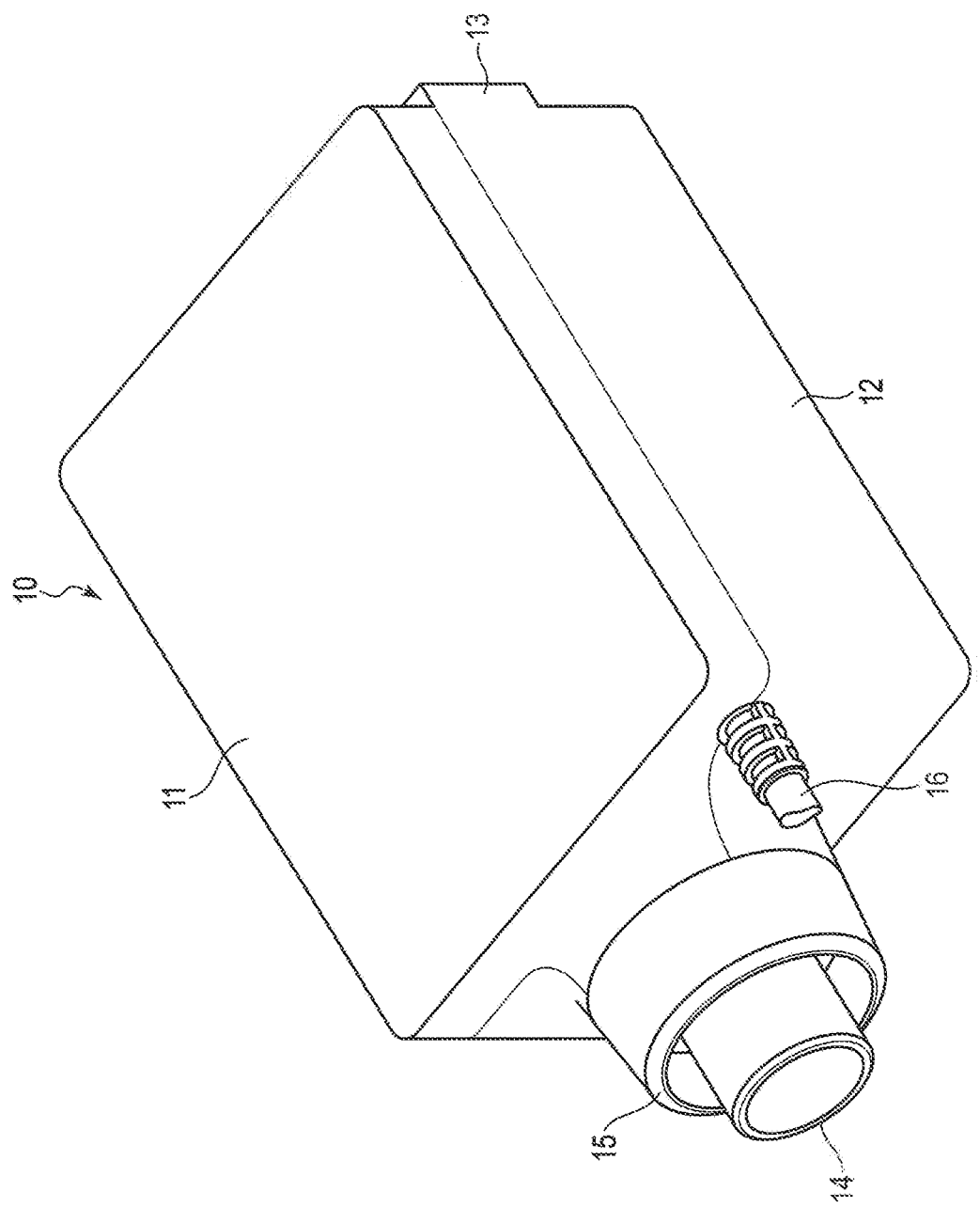
FIG. 1 is a perspective view showing a CPAP device according to the embodiment.

The drawings described herein are for illustration purposes only and are not intended to limit the scope of the present disclosure in any way.

DETAILED DESCRIPTION

The following description is merely exemplary in nature and is not intended to limit the present disclosure, application, or uses. It should be understood that throughout the drawings, corresponding reference numerals indicate like or corresponding parts and features.

An embodiment of the present invention will be described below with reference to the accompanying drawings. Elements like or similar to those disclosed in the embodiment are denoted by similar reference numbers.

In FIG. 1, a CPAP device 10 serving as an air blowing unit is provided with a first case 11 and second case 12, and inside the first case 11 and second case 12, a fan to be described later is provided. In the side surface of the second case 12, a fresh air inlet 13 is provided, and on the side surfaces of the first case 11 and second case 12, a discharge unit 15 including an air outlet 14 is provided. The air sucked in from the air inlet 13 is discharged from the air outlet 14 at fixed pressure. An end of a pipe not shown is attached to the air outlet 14. For example, a mask or nasal cannula not shown is provided at the other end of the pipe, and the mask or nasal cannula is fitted on the nose of the patient. At a position on the side surfaces of the first case 11 and second case 12, and in the vicinity of the discharge unit 15, various cables 16 for the electric power source and interface are provided.

FIG. 2 shows the state where the first case 11 of FIG. 1 is removed. Inside the second case 12, a fan unit 17 is provided. The structure of the fan unit 17 will be described later. An air inlet 17a (shown in FIG. 4) of the fan unit 17 communicates with the air inlet 13 of the second case 12, and blowout opening 17b is connected to the discharge unit 15 through a joint 18. The blowout opening 17b, joint 18, discharge unit 15, and air outlet 14 constitute a flow path PT of the airflow shown in FIG. 4. Inside the joint 18, a straightening plate 31 and pressure difference generating member 32 configured to generate a pressure difference in the airflow both of which will be described later are arranged.

One ends of a first tube 19, second tube 20, and third tube 21 are provided in the discharge unit 15 and joint 18. The other ends of the first tube 19 and second tube 20 are connected to a differential pressure sensor 24 configured to detect a pressure difference through connectors 22 and 23. The first tube 19 is a tube configured to guide the pressure (high pressure) on the upstream side of the pressure difference generating member to be described later to the differential pressure sensor 24, and second tube 20 is a tube configured to guide the pressure (low pressure) on the downstream side of the pressure difference generating member to the differential pressure sensor 24.

The other end of the third tube 21 is connected to a pressure sensor 26 to detect pressure through a connector 25. The third tube is a tube configured to guide the pressure (low pressure) on the downstream side of the pressure difference generating member to be described later to the pressure sensor 26. To the pressure sensor 26, furthermore, one end of a fourth tube 27 is connected. At the other end of the fourth tube 27, a connection opening 28 is provided. The connection opening 28 is arranged at the bottom part of the second case 12, and is opened to the atmosphere. That is, the fourth tube 27 and connection opening 28 open the inside of the pressure sensor 26 to the atmosphere.

The fan unit 17, differential pressure sensor 24, and pressure sensor 26 are arranged on a printed board 29. To the printed board 29, furthermore, the various cables 16 for the electric power source and interface, power switch 30, controller to be described later, and the like are connected.

FIG. 3 schematically shows the configuration of the control system of the CPAP device 10.

The differential pressure sensor 24, pressure sensor 26, fan unit 17, and power switch 30 are connected to a controller 40. The controller 40 calculates a flow rate of an airflow produced from the fan unit 17 on the basis of a pressure difference detected by the differential pressure sensor 24. Furthermore, the controller 40 controls the rotational speed of the fan unit 17 on the basis of the calculated flow rate of the airflow and pressure of the airflow detected by the pressure sensor 26, and makes the fan unit 17 discharge an airflow of a flow rate and pressure which are set in advance from the air outlet 14.

FIG. 4 is a view showing part of FIG. 2 in an extracting manner. The fan unit 17 is constituted of, for example, a turbofan serving as a centrifugal fan (blower). The fan unit 17 is provided with the air inlet 17a, blowout opening 17b, rotating shaft 17d of a motor 17c, and turbo-type fan 17e attached to the rotating shaft 17d. The blowout opening 17b is arranged in a direction perpendicular to the air inlet 17a.

The blowout opening 17b of the fan unit 17 is provided with the joint 18, and the joint 18 is provided with the discharge unit 15. The blowout opening 17b of the fan unit 17, joint 18, and discharge unit 15 constitute the flow path PT through which the airflow produced from the fan unit 17 is made to flow.

Inside the joint 18, the straightening plate 31 and pressure difference generating member 32 are provided. The straightening plate 31 straightens the airflow inside the flow path PT. The pressure difference generating member 32 causes a pressure difference in the airflow inside the flow path PT. The pressure difference generating member 32 is arranged on the discharge unit 15 side of the joint 18, and the straightening plate 31 is arranged on the fan unit 17 side of the joint 18. That is, the straightening plate 31 is arranged between the pressure difference generating member 32 and fan unit 17, and straightens the airflow on the upstream side of the pressure difference generating member 32.

Figure 5:
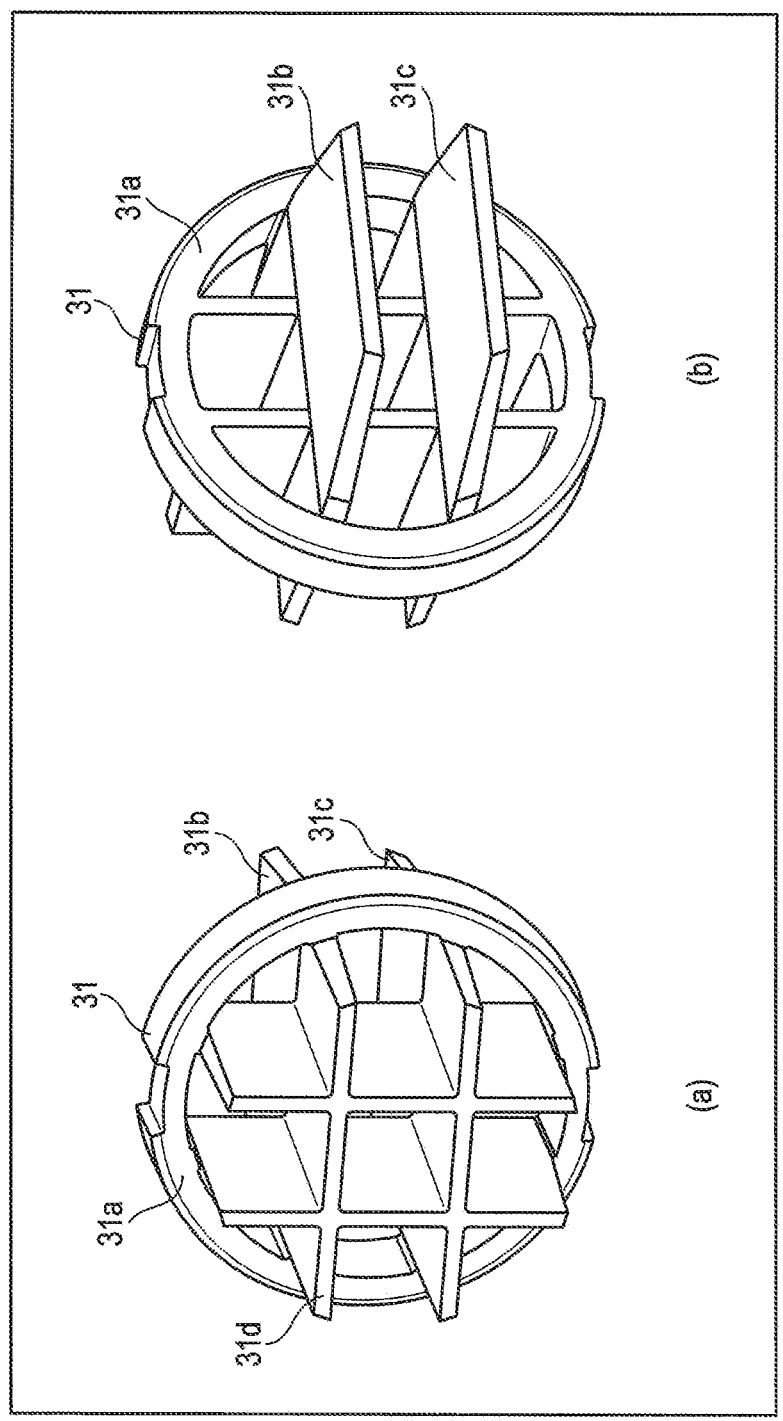
FIG. 5 (a) is a perspective view showing a straightening plate according to this embodiment, and FIG. 5 (b) is a perspective view showing the straightening plate viewed from a direction different from FIG. 5 (a).

FIG. 5 (a) and FIG. 5 (b) show an example of the straightening plate 31. The straightening plate 31 is provided with an annular frame body 31a, and, for example, first fin 31b, second fin 31c, and lattice-like third fin 31d which are provided on the frame body 31a. As shown in FIG. 5 (a), the third fin 31d is provided on the one surface side of the frame body 31a and, as shown in FIG. 5 (b), the first fin 31b and second fin 31c are arranged on the other surface side of the frame body 31a with a predetermined interval held between them and in parallel with each other.

The straightening plate 31 is arranged inside the flow path PT in such a manner that the first fin 31b and second fin 31c are positioned on the upstream side of the flow path PT, and third fin 31d is positioned on the downstream side of the flow path as shown in FIG. 4.

As will be described later, it is desirable that the first fin 31b and second fin 31c be arranged in a direction perpendicular to the rotating shaft of the fan unit 17. By arranging the first fin 31*b* and second fin 31*c* in this manner, it is possible to efficiently reduce eddies included in the airflow produced by the thin-type fan unit 17, and downsize the CPAP device 10.

FIG. 6 (*a*) and FIG. 6 (*b*) show an example of the pressure difference generating member 32. As shown in FIG. 6 (*a*), the pressure difference generating member 32 is provided with a pathway section 32*b* of, for example, a honeycomb structure including a plurality of opening sections 32*a*, flange 32*c* provided around the pathway section 32*b*, cylindrical first connection section 32*d*, second connection section 32*e*, and third connection section 32*f* which are part of the flange 32*c*, and are provided on the surface of the flange 32*c* on the straightening plate 31 side. As will be described later, to the first connection section 32*d*, the first tube 19 is connected, to the second connection section 32*e*, the second tube 20 is connected, and to the third connection section 32*f*, the third tube 21 is connected.

The second connection section 32*e* and third connection section 32*f* respectively communicate with opening sections 32*h* and 32*g* provided in the flange 32*c*. That is, the second connection section 32*e* and third connection section 32*f* communicate with the surface of the flange 32*c* opposite to the surface thereof on the straightening plate 31 side respectively through the opening sections 32*h* and 32*g*. Accordingly, when the second tube 20 is connected to the second connection section 32*e*, and the third tube 21 is connected to the third connection section 32*f*, the pressure inside the second tube 20 and third tube 21 becomes equal to the pressure on the air outlet 14 side of the pressure difference generating member 32.

On the other hand, as shown in FIG. 6 (*b*), the first connection section 32*d* is not made to communicate with the surface of the flange 32*c* opposite to the surface thereof on the straightening plate 31 side unlike the second connection section 32*e* and third connection section 32*f*. The first connection section 32*d* includes a first section 32*d*-1 to which the aforementioned first tube 19 is connected, and second section 32*d*-2 having an outer diameter greater than the first section 32*d*-1 and, furthermore, a slit 32*d*-3 is provided in the side surfaces of the first section 32*d* 1 and second section 32*d*-2. Accordingly, when the first tube 19 is fitted on the first section 32*d*-1, the portion of the second section 32*d*-2 is not covered with the first tube 19 and the slit 32*d*-3 is exposed. Accordingly, the pressure inside the first tube 19 becomes equal to the pressure on the straightening plate 31 side of the pressure difference generating member 32.

Figure 7:
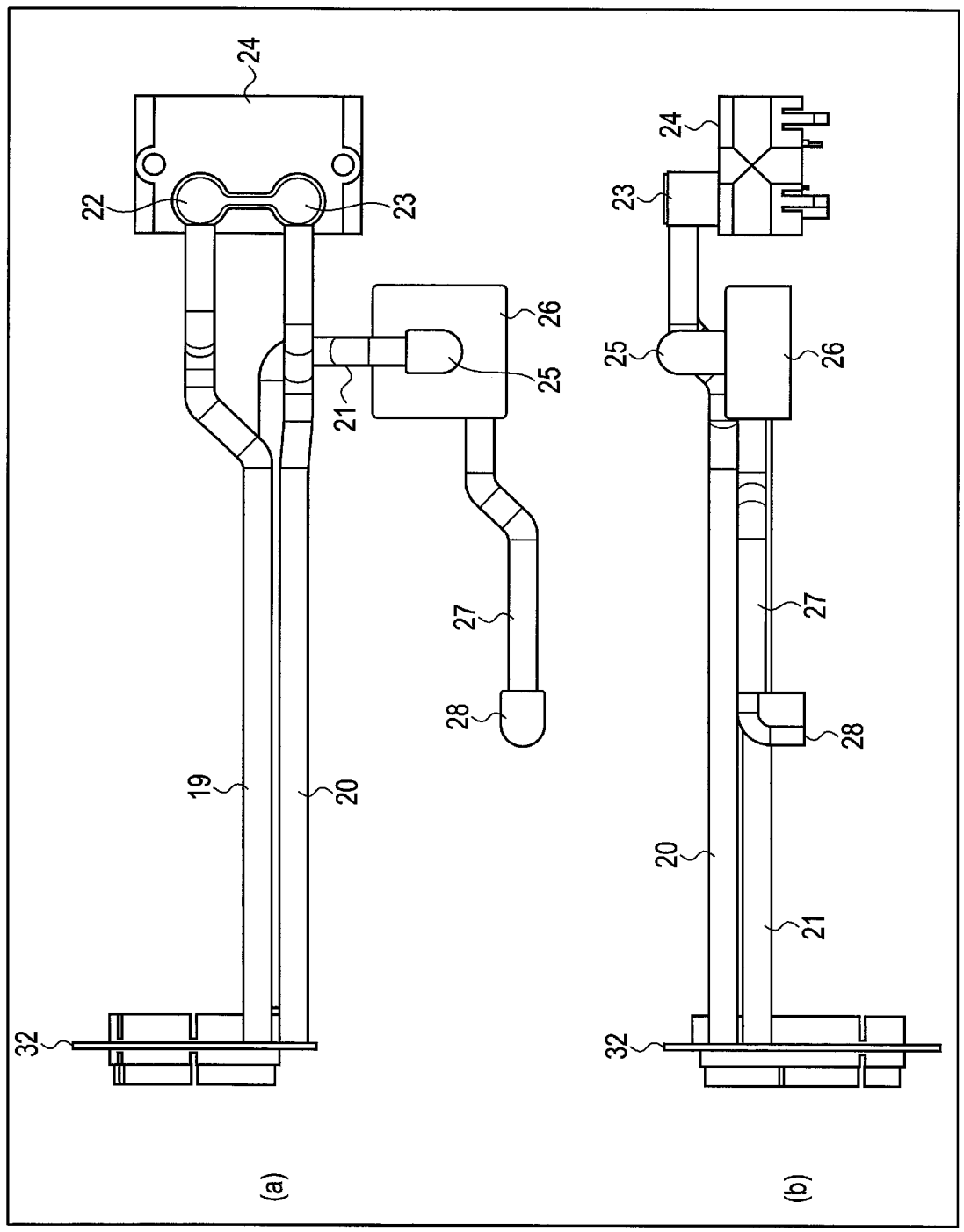
FIG. 7 (a) is a top view showing relationships between the pressure difference generating member, differential pressure sensor, and pressure sensor, and FIG. 7 (b) is a side view of FIG. 7 (a).

FIG. 7 (*a*) and FIG. 7 (*b*) show the state where the first tube 19, second tube 20, and third tube 21 are attached to the pressure difference generating member 32. The first tube 19 connected to the first connection section 32*d* guides the pressure on the straightening plate 31 side of the pressure difference generating member 32 to the differential pressure sensor 24, and second tube 20 connected to the second connection section 32*e* guides the pressure on the air outlet 14 side of the pressure difference generating member 32 to the differential pressure sensor 24. Accordingly, the differential pressure sensor 24 can detect a difference between the pressure on the upstream side of the pressure difference generating member 32 and pressure on the downstream side thereof.

Further, the third tube 21 connected to the third connection section 32*f* guides the pressure on the air outlet 14 side of the pressure difference generating member 32 to the pressure sensor 26. Accordingly, the pressure sensor 26 can detect the pressure on the downstream side of the pressure difference generating member 32.

Figure 8:
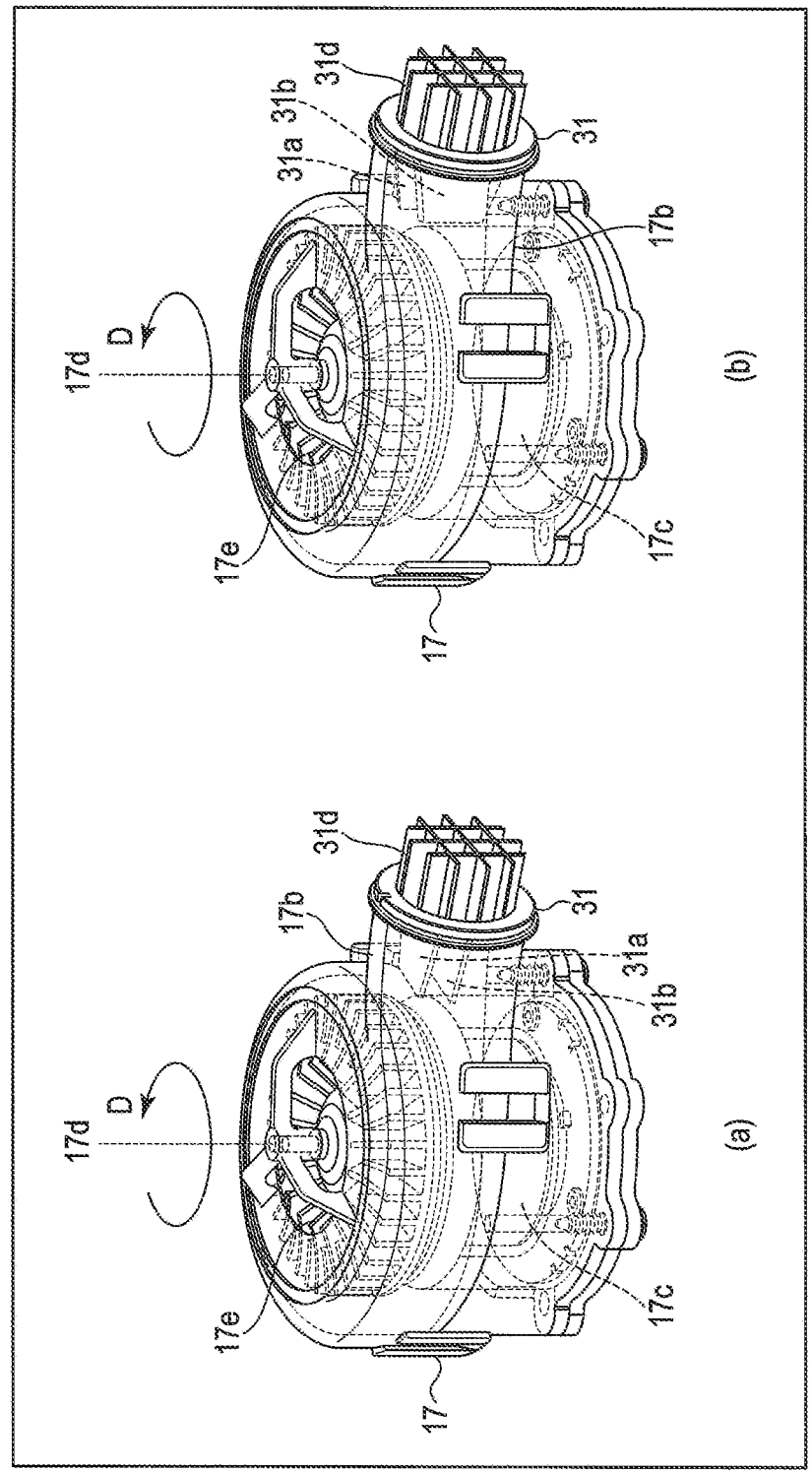
FIG. 8 (a) is a perspective view showing a relationship between the fan unit and straightening plate, and FIG. 8 (b) is a perspective view showing a relationship between the fan unit and straightening plate, the relationship being different from FIG. 8 (a).
Figure 9:
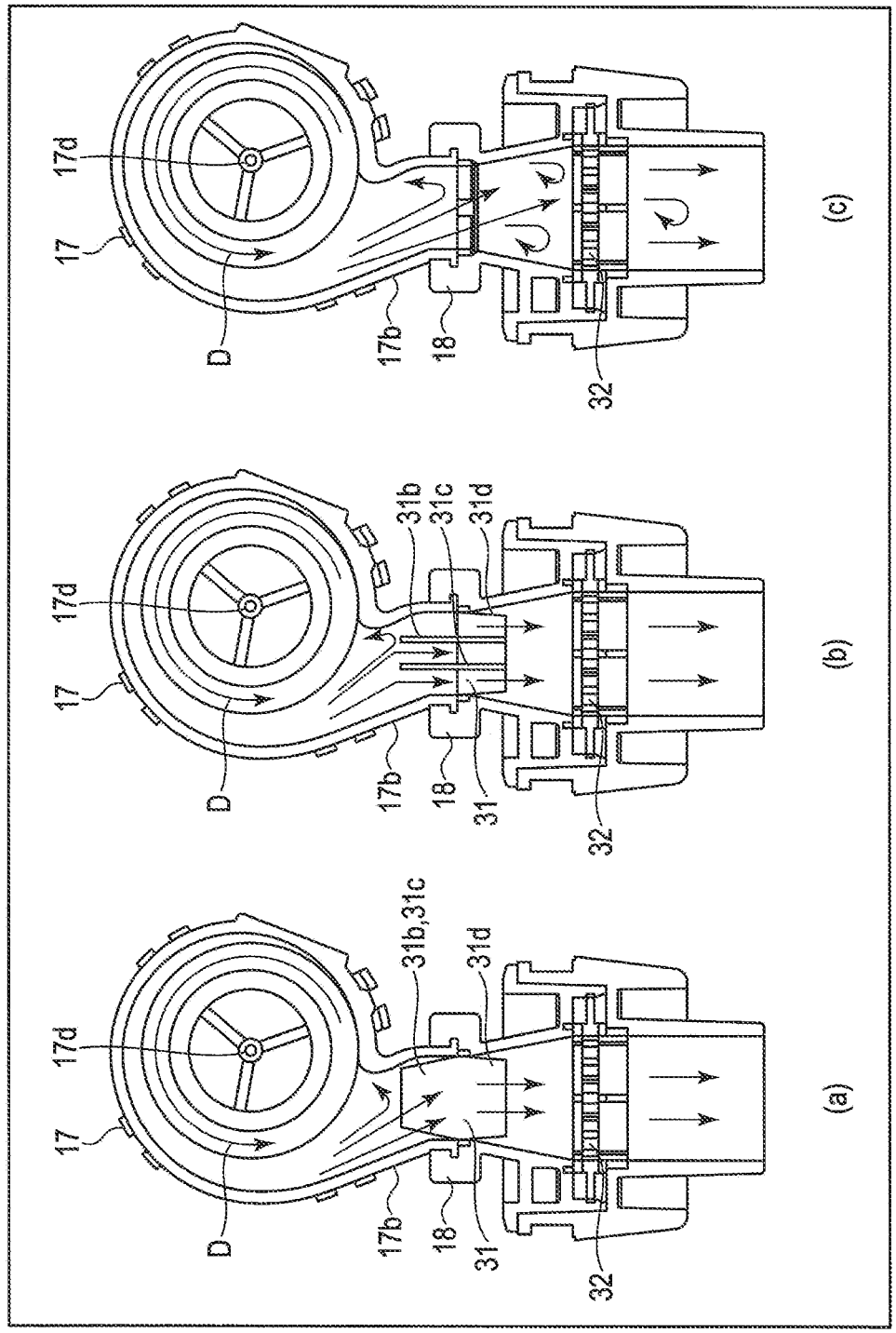
FIG. 9 (a) is a view showing an example of an airflow corresponding to FIG. 8 (a), FIG. 9 (b) is a view showing an example of an airflow corresponding to FIG. 8 (b), and FIG. 9 (c) is a view showing an example of an airflow of a case where no straightening plate is provided.

FIG. 8 (*a*), FIG. 8 (*b*), FIG. 9 (*a*), and FIG. 9 (*b*) respectively show examples of arrangement of the straightening plate 31 relative to the fan unit 17. In order to aim at downsizing of the device shape/size, as shown in FIG. 9 (*a*) and FIG. 9 (*b*), the blowout opening 17*b* of the fan unit 17 is obliquely attached to the joint 18, and the airflow produced by the fan unit 17 is made to obliquely flow into the space of the first fin 31*b* and second fin 31*c* of the straightening plate 31.

In the case of the example shown in FIG. 8 (*a*) or FIG. 9 (*a*), the first fin 31*b* and second fin 31*c* of the straightening plate 31 are arranged in the direction perpendicular to the rotating shaft 17*d* of the motor 17*c* of the fan unit 17.

In the case of the example shown in FIG. 8 (*b*) or FIG. 9 (*b*), the first fin 31*b* and second fin 31*c* of the straightening plate 31 are arranged in parallel with the rotating shaft 17*d* of the fan unit 17. In other words, the first fin 31*b* and second fin 31*c* of the straightening plate 31 are arranged perpendicular to the rotational direction D of the motor 17*c*.

When the first fin 31*b* and second fin 31*c* of the straightening plate 31 are arranged in the direction perpendicular to the rotating shaft 17*d* of the motor 17*c* of the fan unit 17 as shown in FIG. 8 (*a*) and FIG. 9 (*a*), the airflow produced by the fan unit 17 obliquely flows into the space of the straightening plate 31 along the first fin 31*b* and second fin 31*c* of the straightening plate 31. Accordingly, the airflow produced by the fan unit 17 smoothly flows into the space of the straightening plate 31. Thereafter, the airflow is changed by the lattice-like third fin 31*d* in the angle thereof around the axis thereof, and flows into the pressure difference generating member 32 almost perpendicularly thereto.

When the first fin 31*b* and second fin 31*c* of the straightening plate 31 are arranged in the direction (perpendicular to the rotational direction D of the motor 17*c*) parallel to the rotating shaft 17*d* of the motor 17*c* of the fan unit 17 as shown in FIG. 8 (*b*) and FIG. 9 (*b*), the airflow produced by the fan unit 17 strikes against the first fin 31*b* and second fin 31*c* to thereby be changed in the flowing direction and then flows into the space of the third fin 31*d*. In this case too, as in the examples shown in FIG. 8 (*a*) and FIG. 9 (*a*), the airflow which has passed through the straightening plate 31 flows into the pressure difference generating member 32 almost perpendicularly thereto.

As shown in FIG. 8 (*a*), FIG. 8 (*b*), FIG. 9 (*a*), and FIG. 9 (*b*), by straightening the airflow produced by the fan unit 17 by means of the straightening plate 31, it is possible to remove almost all the eddies included in the airflow produced by the fan unit 17. Accordingly, it is possible to send an airflow including no eddies into the pressure difference generating member 32. Accordingly, it is possible to remove eddies from the portions of the airflow on the upstream side and downstream side of the pressure difference generating member 32, and improve the detection accuracy of the differential pressure sensor 24.

It should be noted that when the straightening plate 31 is not used as shown in FIG. 9 (*c*), the airflow produced by the fan unit 17 and including eddies obliquely flows into the pressure difference generating member 32 and, eddies are included also in the airflow which has passed through the pressure difference generating member 32. For this reason, it is difficult to improve the detection accuracy of the differential pressure sensor 24.

Figure 10:
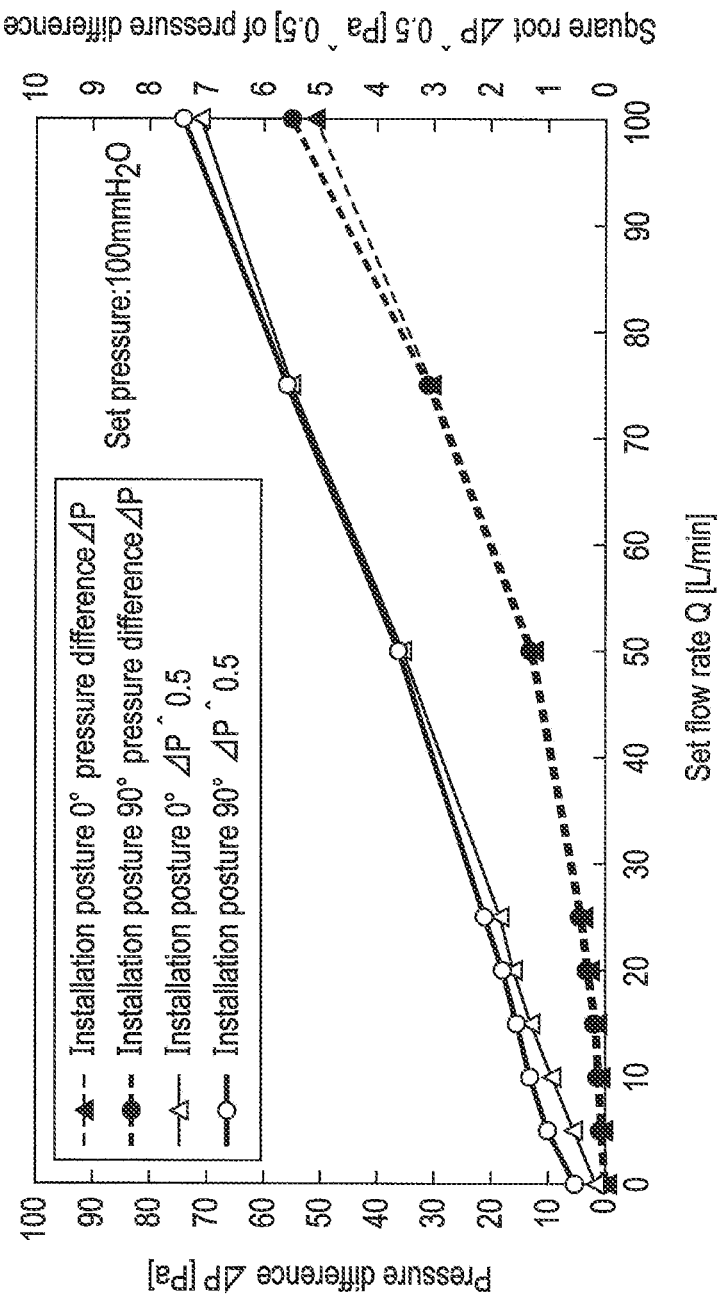
FIG. 10 is a characteristic graph showing the installation position of the straightening plate, pressure difference, and square root of the pressure difference.

FIG. 10 shows the relationships between the installation posture of the straightening plate 31, pressure difference ΔP [Pa], and square root ΔP0.5 [Pa0.5] of the pressure difference. More specifically, FIG. 10 shows, in the case where the set pressure P of the airflow output from the CPAP device 10 is, for example, 200 mm H2O, the relationships of the pressure difference ΔP [Pa] and square root ΔP0.5 [Pa0.5] of the pressure difference with the set flow rate. In FIG. 10, the solid line indicates the square root of the pressure difference, and broken line indicates the pressure difference. Further, the characteristic curve of triangular marks is that of the case where the installation posture corresponds to an angle 0° (the first fin 31b and second fin 31c are in the direction perpendicular to the rotating shaft 17d of the fan unit 17 as shown in FIG. 8 (a) and FIG. 9 (a)) and, characteristic curve of circular marks is that of the case where the installation posture corresponds to an angle 90° (the first fin 31b and second fin 31c are perpendicular to the rotational direction of the fan unit 17 and parallel to the rotating shaft 17d as shown in FIG. 8 (b) and FIG. 9 (b)).

As is evident from the characteristics of the square root of the pressure difference indicated by the solid line, when the installation posture of the straightening plate 31 corresponds to an angle 90° (characteristics of the circular marks), slight variations in the pressure difference occur in the region in which the set flow rate is less than or equal to 20 L/min as compared with the case where the installation posture corresponds to an angle 0° (characteristics of the triangular marks). Particularly, it can be seen that at the point at which the set flow rate is 0 L/min, when the installation posture of the straightening plate 31 is 90°, a pressure difference occurs. Accordingly, it is desirable that the installation posture of the straightening plate 31 be 0°.

(Advantage)

According to the embodiment described above, the straightening plate 31 is provided between the fan unit 17 and pressure difference generating member 32, whereby the eddies included in the airflow on the upstream side of the pressure difference generating member 32 are reduced. Accordingly, it is possible to further reduce the eddies included in the airflow on the downstream side of the pressure difference generating member 32. Therefore, the eddies included in the airflow on the upstream side of the pressure difference generating member 32 and eddies included in the airflow on the downstream side of the pressure difference generating member are reduced, and hence it is possible to accurately detect the pressure difference by using the pressure difference generating member 32. Accordingly, it is possible to measure the accurate flow rate of the airflow produced from the fan unit 17.

Furthermore, by providing the straightening plate 31 between the fan unit 17 and pressure difference generating member 32, it is possible to arrange the straightening plate 31 in the vicinity of the fan unit 17. Accordingly, it is possible to prevent the size of the CPAP device 10 from becoming larger, and improve the detection accuracy of the pressure difference.

It should be noted that the frame body 31a of the straightening plate 31 is provided with two fins including the first fin 31b and second fin 31c. However, the number of fins is not limited to two, and the number of fins may be one or three or more.

Further, the fan unit 17 is not limited to the centrifugal fan configured to send air in the direction perpendicular to the inlet direction, and an axial flow fan configured to send air in the direction parallel to the inlet direction can also be applied. When the axial flow fan is used, the direction of the rotating shaft of the fan is identical to the direction of the airflow, and hence the installation posture of the straightening plate 31 may be any one of 0° and 90° relative to the rotating shaft of the fan. That is, it is sufficient if the first fin 31b and second fin 31c of the straightening plate 31 are parallel to the rotating shaft of the fan, and are parallel to the direction of the rotating shaft. In this case too, it is possible to reduce the eddies included in the airflow on the upstream side of the pressure difference generating member 32 by means of the straightening plate 31.

The invention is not limited to the foregoing embodiment but in the implementation stage various changes and modifications of its components may be made without departing from the scope of the present invention. Also, the components disclosed in the embodiment may be assembled in any combination for embodying the present invention. For example, some of the components may be omitted from all the components disclosed in the embodiment. Further, components in different embodiments may be appropriately combined.

The CPAP device according to the embodiment of the present invention can be applied to medical treatment for a sleep apnea syndrome.

Unless otherwise expressly indicated herein, all numerical values indicating mechanical/thermal properties, compositional percentages, dimensions and/or tolerances, or other characteristics are to be understood as modified by the word "about" or "approximately" in describing the scope of the present disclosure. This modification is desired for various reasons including industrial practice, manufacturing technology, and testing capability.

As used herein, the phrase at least one of A, B, and C should be construed to mean a logical (A OR B OR C), using a non-exclusive logical OR, and should not be construed to mean "at least one of A, at least one of B, and at least one of C."

The description of the disclosure is merely exemplary in nature and, thus, variations that do not depart from the substance of the disclosure are intended to be within the scope of the disclosure. Such variations are not to be regarded as a departure from the spirit and scope of the disclosure.

What is claimed is:

1. A CPAP device comprising:
    a centrifugal fan configured to produce an airflow;
    a motor with a rotating shaft, the rotating shaft being coupled to the fan and configured to drive the fan;
    a pressure difference generating member configured to pass the airflow through and cause a pressure difference in the airflow;
    a sensor configured to detect a pressure difference between the air pressure on the upstream side of the pressure difference generating member and the air pressure on the downstream side of the pressure difference generating member; and
    a straightening plate provided between the centrifugal fan and the pressure difference generating member and configured to straighten the airflow produced by the centrifugal fan, wherein
    the straightening plate includes:
        at least one fin positioned in the upstream of the airflow, and arranged in a direction perpendicular to the rotating shaft of the motor, and
        a lattice-like fin which is arranged on the downstream side of the at least one fin, and through which the airflow passing through the at least one fin passes.

2. The CPAP device of claim 1, wherein a number of the at least one fin is more than two.

3. The CPAP device of claim 1, wherein
the centrifugal fan is arranged in a fan unit including a blowout opening, the blowout opening is arranged on upstream side of the straightening plate and arranged in obliquely in a plane perpendicular to the rotating shaft of the motor.

4. The CPAP device of claim 3, wherein the straightening plate flows the airflow in obliquely from the blowout opening to the at least one fin and to the pressure difference generating member in perpendicular.

* * * * *